US011643695B2

(12) United States Patent
Huang et al.

(10) Patent No.: US 11,643,695 B2
(45) Date of Patent: May 9, 2023

(54) *SINIPERCA CHUATSI* IL-6 GENE AND DETECTION METHOD OF DISEASE-RESISTANT SNP MARKER THEREOF

(71) Applicant: SOOCHOW UNIVERSITY, Suzhou (CN)

(72) Inventors: Hezhong Huang, Suzhou (CN); Yao Lu, Suzhou (CN); Ruiming Jin, Suzhou (CN); Ze Li, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 202 days.

(21) Appl. No.: 17/190,649

(22) Filed: Mar. 3, 2021

(65) Prior Publication Data
US 2021/0189508 A1 Jun. 24, 2021

Related U.S. Application Data

(62) Division of application No. 16/504,371, filed on Jul. 8, 2019, now Pat. No. 10,988,814.

(30) Foreign Application Priority Data

Jul. 6, 2018 (CN) .......................... 201810734995.2

(51) Int. Cl.
*C12Q 1/68* (2018.01)
*C12Q 1/6888* (2018.01)
*C07K 14/54* (2006.01)

(52) U.S. Cl.
CPC ........ *C12Q 1/6888* (2013.01); *C07K 14/5412* (2013.01); *C12Q 2600/124* (2013.01); *C12Q 2600/156* (2013.01)

(58) Field of Classification Search
None
See application file for complete search history.

(56) References Cited

PUBLICATIONS

SNP, definition. Scitable by nature Education, copyright 2014. Obtained from https://www.nature.com/scitable/definition/snp-295/ on Nov. 15, 2022. 2 pages. (Year: 2014).*
Bo-Hye Nam et al., Molecular cloning and characterisation of the flounder (*Paralichths olivaceus*) interleukin-6 gene, Fish & Shellfish Immunology 23 (2007) 231-236.
Wenlong Li, PKR gene cloning and expression study of interferon system genes in Sinipera chuatsi, Soochow University Master Degree Thesis, May 2016.
Chan Li, Molecular and expression characterizations of some disease-resistant chemokines in large yellow croaker, Karimichthys crocea, Jimei University Master Thesis, Jun. 3, 2012.

* cited by examiner

*Primary Examiner* — Juliet C Switzer
(74) *Attorney, Agent, or Firm* — SZDC Law P.C.

(57) ABSTRACT

The invention provides a *Siniperca chuatsi* IL-6 gene and a detection method for a disease-resistant SNP marker. A cDNA sequence of *S. chuatsi* IL-6 gene is cloned, as shown in SEQ ID NO: 1. A IL-6 gene gDNA sequence containing an intron of the *S. chuatsi* IL-6 gene is cloned, as shown in SEQ ID NO: 2. A primer for amplifying a disease-resistant SNP locus is designed according to IL-6 gDNA sequence, and *S. chuatsi* IL-6 gene is amplified to obtain an amplification product which is sequenced, and the SNPs loci relevant to virus disease-resistance are found out and the SNP locus is determined according to DNA peak profile. The IL-6 cDNA full-length sequence and IL-6 gDNA full-length sequence are cloned firstly. The SNP locus relevant to virus disease resistance of *S. chuatsi* IL-6 gene is detected, thereby providing a new method for breeding of *S. chuatsi*.

3 Claims, 4 Drawing Sheets

Specification includes a Sequence Listing.

SEQUENCE LISTING

```
<160> NUMBER OF SEQ ID NOS: 17

<210> SEQ ID NO 1
<211> LENGTH: 1357
<212> TYPE: DNA
<213> ORGANISM: Siniperca chuatsi

<400> SEQUENCE: 1
taacccaaag aggcaggtga ctcctcagga caggtgactc ctcagggcag gtgactcctc      60
agggcctgac agccctcagc atcagcggaa actcaacaag tgcttcgcag ctgcgcaaca     120
tgccctataa actcaacgcg tacctgctct ctgcagtgat gctggcagct ccgctgcagt     180
gcgctcccgg agctccagct gaatacgcgc ccaccgacag cccggcaggt gactcctcag     240
gtgaggagga ggaggaggag aggccctctg aactactgag cgtctccaag gagttggagt     300
tgatccttgg cgcaaccaaa cgccacaggg aggagtttga agatgaattc caaactgagg     360
```

```
tgaaatatga ctttctgagg cactacacag tctcctcact tccagcaagc tgcccttact    420
ccaacttcag caaggaggct tgtctccaca ggttggccca tgggctgcct atttacagag    480
ttcttctcaa gtatgtggag aaggagtgcc ccagcagccg gatcccctca gaggccagat    540
tctacggagg cctcctgatc agtcagatca agaaaaagat gaagaaccct gaacaggtca    600
cggcactcac cagcagccag gagaataagc tgctgaagga cctcgacaac cccgacactt    660
tccacagaaa gatgacggca cacagcatcc tgcgccagct ccactacttc cttgtcgacg    720
gcaaaagagc tattaaaaaa agggagttca gagcaagtat ggccaacagg ggcatggcac    780
ctgttacttt ctattaccaa agttaaaaaa tatgaaggta ttaaaaatca cttattacgt    840
aatacctcag ggaaattgga tggtgttaaa agtacatgtt ctgagtacac caactgtact    900
gttggtatag tgggtctatc aatctatgac tgtgtaaatc ttacagacct caaggcttga    960
accaaccact attacacaac ttatttaacc tatttatgct tagtgaaaag tgatatttat   1020
tagtcatagg aaaatccatg attgtgggtt tcttgcacta aaaatgcaat ttgtacttga   1080
ttttagagtt ggttaatttc ttgattgtta ttacttgagc agcattgtta ggaaaagcaa   1140
taattgcatc atctattttt ataaacaata agtttatatt tacagtactt ttaactgtca   1200
tttatttaca actattatta ttaaactgaa tttgctgttc atttaattac aatgcaatga   1260
gccgtgcttt gaaggcaaaa caaccaattc tgtaaatatg cagaaataaa aaaaaaaact   1320
atttgctaaa aaaaaaaaaa aaaaaaaaaa aaaaaaa                            1357
```

<210> SEQ ID NO 2
<211> LENGTH: 2382
<212> TYPE: DNA
<213> ORGANISM: Siniperca chuatsi

<400> SEQUENCE: 2

```
taacccaaag aggcaggtga ctcctcagga caggtgactc ctcagggcag gtgactcctc     60
agggcctgac agccctcagc atcagcggaa actcaacaag tgcttcgcag ctgcgcaaca    120
tgccctataa actcagtaag tggtttgcac gctgcggcgc gcacgtttcc cttgtttctt    180
cctcttttgt tgttcattca gtcattcatg ctttacgtcc ccgcacagac gcgtacctgc    240
tctctgcagt gatgctggca gctctgctgc agtgcgctcc cggagctcca gctgaatacg    300
cgcccaccga cagcccggca ggtgactcct caggtgagga ggaggaggag gagaggccct    360
ctgaactact gagcgtctcc aaggagttgg agttgatcct tggcgcaacc aaacgccaca    420
gggaggaggt aagcgcgtta tcttccagga atgtcagtga actatagtat ttcagttgct    480
tacatcagta tcttattttc tgagcattta taaagtaaac tgcactcctg acctccatgc    540
tgtttctttc atcatttccc cttatcagtt tgaagatgaa ttccaaactg aggtgaaata    600
tgactttctg aggcactaca cagtctcctc acttccagca agctgccctt actccaactt    660
cagcaaggta tagttgtgtc tcctcctttg tcgtcctgtt agccgataaa agaaactggg    720
tggtggggtt catttgagca ctgacagtga ttttctttcc tctctccagg aggcttgtct    780
ccacaggttg gcccatgggc tgcctatttta cagagttctt ctcaagtatg tggagaagga    840
gtgccccagc agccggatcc cctcagaggc cagattctac ggaggcctcc tgatcagtca    900
gatcaaagaa aaggtgggtc tgagatgcta aactaaaaat catatttcaa tttgtagctc    960
tgctgtggtg gcctttgtat cagtctctct ctggtcatta ttgcttttga tctggctcac   1020 ttttttcacca tctttgttat agccagtggt ggaagaagta tttagatcct gtagcaatac   1080
aacactataa aaatactcca ttatgagtaa aagccctgcc tcctgtcagt gttacattat   1140
```

```
tatattttac attatcacat tattattact gatgccttaa tgtgttagtt atactgttat    1200
agctggtaaa ggtggaatta attttacttt gtatactatt gggtagttta acaatggcag    1260
tgccttgtat ttttataaac tcctcatgag tttcgtatct gcaaagtaac tactggagtg    1320
gaagtagcac aaaatggaaa tacccaagca aagtacctca aaactgtact taagctcagt    1380
acttgagtaa tgtacttact tacattccac cactggttat agctcagtta ttagattccc    1440
tacttataat ttcttttgcg tttaatttct gttgcgtaaa tgtctgattt tgtcttctat    1500
ttttgatcac gtctaattgt aaatgacttt gtaatggatt ggattattat tacaatacag    1560
cactgcatag tcctataata ccactgtcac ttctgcccca cagatgaaga accctgaaca    1620
ggtcacggca ctcaccagca gccaggagaa taagctgctg aaggacctcg acaaccccga    1680
cactttccac agaaagatga cggcacacag catcctgcgc cagctccact acttccttgt    1740
cgacggcaaa agagctatta aaaaaggga gttcagagca agtatggcca cagggggcat    1800
ggcacctgtt actttctatt accaaaagtt aaaaatatga aggtattaaa aatcacttat    1860
tacgtaatac ctcagggaaa ttggatggtg ttaaaagtac atgttctgag tacaccaact    1920
gtactgttgg tatagtgggt ctatcaatct atgactgtgt aaatcttaca gacctcaagg    1980
cttgaaccaa ccactattac acaacttatt taacctattt atgcttagtg aaaagtgata    2040
tttattagtc ataggaaaat ccatgattgt gggtttcttg cactaaaaat gcaatttgta    2100
cttgatttta gagttggtta atttcttgat tgttattact tgagcagcat tgttaggaaa    2160
agcaataatt gcatcatcta tttttataaa caataagttt atatttacag tacttttaac    2220
tgtcatttat ttacaactat tattattaaa ctgaatttgc tgttcattta attacaatgc    2280
aatgagccgt gctttgaagg caaacaacc aattctgtaa atatgcagaa ataaaaaaaa    2340
aaactatttg ctaaaaaaaa aaaaaaaaa aaaaaaaaa aa                         2382
```

<210> SEQ ID NO 3
<211> LENGTH: 231
<212> TYPE: PRT
<213> ORGANISM: Siniperca chuatsi

<400> SEQUENCE: 3

Met Pro Tyr Lys Leu Asn Ala Tyr Leu Leu Ser Ala Val Met Leu Ala
1               5                   10                  15

Ala Pro Leu Gln Cys Ala Pro Gly Ala Pro Ala Glu Tyr Ala Pro Thr
            20                  25                  30

Asp Ser Pro Ala Gly Asp Ser Gly Glu Glu Glu Glu Glu Arg
        35                  40                  45

Pro Ser Glu Leu Leu Ser Val Ser Lys Glu Leu Glu Leu Ile Leu Gly
    50                  55                  60

Ala Thr Lys Arg His Arg Glu Glu Phe Glu Asp Glu Phe Gln Thr Glu
65                  70                  75                  80

Val Lys Tyr Asp Phe Leu Arg His Tyr Thr Val Ser Ser Leu Pro Ala
                85                  90                  95

Ser Cys Pro Tyr Ser Asn Phe Ser Lys Glu Ala Cys Leu His Arg Leu
            100                 105                 110

Ala His Gly Leu Pro Ile Tyr Arg Val Leu Leu Lys Tyr Val Glu Lys
        115                 120                 125

Glu Cys Pro Ser Ser Arg Ile Pro Ser Glu Ala Arg Phe Tyr Gly Gly
    130                 135                 140

Leu Ile Ser Gln Ile Lys Glu Lys Met Lys Asn Pro Glu Gln Val
145                 150                 155                 160

Thr Ala Leu Thr Ser Ser Gln Glu Asn Lys Leu Leu Lys Asp Leu Asp
                165                 170                 175

Asn Pro Asp Thr Phe His Arg Lys Met Thr Ala His Ser Ile Leu Arg
            180                 185                 190

Gln Leu His Tyr Phe Leu Val Asp Gly Lys Arg Ala Ile Lys Lys Arg
        195                 200                 205

Glu Phe Arg Ala Ser Met Ala Asn Arg Gly Met Ala Pro Val Thr Phe
210                 215                 220

Tyr Tyr Gln Lys Leu Lys Ile
225                 230

<210> SEQ ID NO 4
<211> LENGTH: 16
<212> TYPE: DNA
<213> ORGANISM: Artificial Sequence
<220> FEATURE:
<223> OTHER INFORMATION: Primer GSP-IL-6-1

<400> SEQUENCE: 4
ctggggcact ccttct                                                      16

<210> SEQ ID NO 5
<211> LENGTH: 18
<212> TYPE: DNA
<213> ORGANISM: Artificial Sequence
<220> FEATURE:
<223> OTHER INFORMATION: Primer GSP-IL-6-2

<400> SEQUENCE: 5
aacctgtgga gacaagcc                                                    18

<210> SEQ ID NO 6
<211> LENGTH: 20
<212> TYPE: DNA
<213> ORGANISM: Artificial Sequence
<220> FEATURE:
<223> OTHER INFORMATION: Primer GSP-IL-6-3

<400> SEQUENCE: 6
ctgaagttgg agtaagggca                                                  20

<210> SEQ ID NO 7
<211> LENGTH: 25
<212> TYPE: DNA
<213> ORGANISM: Artificial Sequence
<220> FEATURE:
<223> OTHER INFORMATION: Primer 3'CDS Primer A

<400> SEQUENCE: 7
aagcagtggt atcaacgcag actac                                            25

<210> SEQ ID NO 8
<211> LENGTH: 25
<212> TYPE: DNA
<213> ORGANISM: Artificial Sequence
<220> FEATURE:
<223> OTHER INFORMATION: Primer GSP-IL-6-4

<400> SEQUENCE: 8
cgccagctcc actacttcct tgtcg                                            25

<210> SEQ ID NO 9
<211> LENGTH: 25
<212> TYPE: DNA
<213> ORGANISM: Artificial Sequence
<220> FEATURE:
<223> OTHER INFORMATION: Primer GSP-IL-6-5

<400> SEQUENCE: 9
aaagggagtt cagagcaagt atggc                                  25

<210> SEQ ID NO 10
<211> LENGTH: 20
<212> TYPE: DNA
<213> ORGANISM: Artificial Sequence
<220> FEATURE:
<223> OTHER INFORMATION: Primer AUAP

<400> SEQUENCE: 10
ggccacgcgt cgactagtac                                        20

<210> SEQ ID NO 11
<211> LENGTH: 22
<212> TYPE: DNA
<213> ORGANISM: Artificial Sequence
<220> FEATURE:
<223> OTHER INFORMATION: Primer UPM

<400> SEQUENCE: 11
ctaatacgac tcactatagg gc                                     22

<210> SEQ ID NO 12
<211> LENGTH: 20
<212> TYPE: DNA
<213> ORGANISM: Artificial Sequence
<220> FEATURE:
<223> OTHER INFORMATION: Primer IL-6-1F

<400> SEQUENCE: 12
ctcagcatca gcggaaactc                                        20

<210> SEQ ID NO 13
<211> LENGTH: 20
<212> TYPE: DNA
<213> ORGANISM: Artificial Sequence
<220> FEATURE:
<223> OTHER INFORMATION: Primer IL-6-1R

<400> SEQUENCE: 13
tgcccctgtt ggccatactt                                        20

<210> SEQ ID NO 14
<211> LENGTH: 20
<212> TYPE: DNA
<213> ORGANISM: Artificial Sequence
<220> FEATURE:
<223> OTHER INFORMATION: Primer IL-6-L1F

<400> SEQUENCE: 14
aacccaaaga ggcaggtgac                                        20

<210> SEQ ID NO 15
<211> LENGTH: 21
<212> TYPE: DNA
<213> ORGANISM: Artificial Sequence
<220> FEATURE:
<223> OTHER INFORMATION: Primer IL-6-L1R

```
<400> SEQUENCE: 15
accatccaat ttccctgagg t                                              21

<210> SEQ ID NO 16
<211> LENGTH: 24
<212> TYPE: DNA
<213> ORGANISM: Siniperca chuatsi

<400> SEQUENCE: 16 agctcttttgccgtcgacaaggaa                                             24

<210> SEQ ID NO 17
<211> LENGTH: 24
<212> TYPE: DNA
<213> ORGANISM: Siniperca chuatsi

<400> SEQUENCE: 17 agctcttttgccatcgacaaggaa                                             24
```

SINIPERCA CHUATSI IL-6 GENE AND DETECTION METHOD OF DISEASE-RESISTANT SNP MARKER THEREOF

This application is a Divisional Application of U.S. Ser. No. 16/504,371, filed on Jul. 8, 2019, which claims priority to Chinese Patent Application No.: 201810734995.2, filed on Jul. 6, 2018, which is incorporated by reference for all purposes as if fully set forth herein.

FIELD OF THE INVENTION

The present invention relates to the fields of aquiculture and biotechnology, and more particularly to *Siniperca chuatsi* (*S. chuatsi*) IL-6 gene and a detection method of a disease-resistant SNP marker thereof.

DESCRIPTION OF THE RELATED ART

As a "prestigious" fish with important economic value in China, *S. chuatsi* occupies an important position in freshwater aquaculture in China. However, under the conditions of large-scale artificial breeding in recent years, the genetical characterization decline of *S. chuatsi* is quite common, which leads to the gradual decline of disease resistance, especially the increasingly rampant viral diseases infected by infectious spleen and kidney necrosis virus. And so far, there is no effective prevention method, which causes serious economic losses every year and seriously restricts the sustainable development of the aquaculture industry.

The existing fish breeding technique is to select fish based on the apparent traits of fish observed by naked eyes, which makes it impossible to correctly select fish from the perspective of genetic differences closely related to apparent traits. It is not only impossible to carry out early breeding, but also difficult to guarantee the offspring characteristics and the breeding is blind, time-consuming and laborious.

Cloning of genes related to disease resistance and screening of disease-resistant germplasm resources by SNP molecular markers are effective means to improve disease resistance of *S. chuatsi* to viruses and other diseases. SNPs, that is, signal nucleotide poly-morphisms. transition, transversion, insertion or deletion of a single base on a gene fragment will lead to SNP polymorphism and disease resistance phenotype differences among individuals.

During the disease-resistant genes, IL-6 (interleukin-6) is a cytokine belonging to interleukin, which can promote the proliferation and differentiation of various cells involved in the immune responses, improve their functions, and inhibit cell apoptosis. However, currently the researches on the cloning and functions of fish IL-6 gene are lack, because the fish has low homology of IL-6 gene sequence with the other species, moreover, the transcription and translation process of IL-6 gene is very unstable when subjected to immunostimulation, and thus causes fewer clones of cDNA library of fish cytokines. Accordingly, cloning of cDNA full-length sequence, gDNA full-length sequence of *S. chuatsi* IL-6 gene is of great significance.

SUMMARY OF THE INVENTION

An object of the invention is to provide a disease-resistant IL-6 gene (interleukin, IL-6) of *S. chuatsi*, intended to solve the problem that the fish has low IL-6 gene homology with other species and some fish lack of IL-6 gene.

Another object of the invention is to provide a detection method of a disease-resistant SNP marker of *S. chuatsi*. The method is based on the IL-6 gene of *S. chuatsi* provided in the invention, wherein single nucleotide polymorphism (SNP) is combined with disease-resistant apparent traits of fish, based on SNP marker (or known as mutation site) of IL-6 of disease-resistant or non-disease-resistant fish, to breed selectively and accurately disease-resistant fish population. The invention can improve the efficiency of breeding of superior breeding, decrease the morbidity and mortality of the breeding fish, and thus increase the economic benefits of fish culture, thereby providing a significant meaning for the progress of fish breeding.

The invention utilizes the following technical solutions:

In one aspect, the invention provides a *S. chuatsi* IL-6 gene having a cDNA sequence shown in SEQ ID NO: 1.

In another aspect, the invention also provides a detection method for a disease-resistant SNP marker based on the above IL-6 gene of *S. chuatsi*, comprising the steps of (1) designing a primer for amplifying a disease-resistant SNP locus according to IL-6 gDNA sequence containing intron of the *S. chuatsi* IL-6 gene, and amplifying the *S. chuatsi* IL-6 gene to obtain an amplification product;

(2) sequencing the amplification product and finding out SNPs loci relevant to virus disease resistance, and determining the SNP locus according to DNA peak profile.

Preferably, in the step (1), the IL-6 gDNA sequence is obtained by designing and amplifying a specific primer for *S. chuatsi* IL-6 gene, and the IL-6 gDNA sequence has a nucleotide sequence shown in SEQ ID NO: 2.

Preferably, the specific primer is:

```
IL-6-1F:
                                (SEQ ID NO: 12)
5'-CTCAGCATCAGCGGAAACTC-3';

IL-6-1R:
                                (SEQ ID NO: 13)
5'-TGCCCCTGTTGGCCATACTT-3';
```

Preferably, in the step (1), rapid amplification of cDNA ends (RACE) is performed to clone the *S. chuatsi* IL-6 gene.

Preferably, in the step (1), the primer for amplifying disease-resistant SNP loci is:

```
IL-6-L1F:
                                (SEQ ID NO: 14)
5'-AACCCAAAGAGGCAGGTGAC-3';
IL-6-L1R:
                                (SEQ ID NO: 15)
5'-ACCATCCAATTTCCCTGAGGT-3'.
```

Preferably, in the step (2), multiple sequence alignment is performed on the sequencing results by DNAMAN software and the suspected SNPs loci are found out, and DNA sequencing chromatogram is observed via Chromas software, single peak is a homozygotic SNP locus, and the nested peak is a heterozygous SNP locus.

Preferably, the SNP marker is located at the 1744 bp of the gDNA sequence *S. chuatsi* having a nucleotide sequence shown in SEQ ID NO: 2, the base at 1744 bp of *S. chuatsi* susceptible to virus is T, and the base at 1744 bp of antivirus *S. chuatsi* is C, the virus is infectious spleen and kidney necrosis virus.

As compared with prior art, the present invention has the following advantages:

(1) In the invention, IL-6 cDNA full-length sequence and IL-6 gDNA full-length sequence of *S. chuatsi* are cloned firstly, thereby providing research basis for resistant breeding of fish;

(2) In the invention, the SNP locus of mandarin fish IL-6 gene relevant to virus disease resistance is detected to provide a new idea for breeding of *S. chuatsi*, this facilitates to promote the genetic breeding process and increase the economic benefits of mandarin fish culture.

DETAILED DESCRIPTION OF THE PREFERRED EMBODIMENTS

Figure 1:
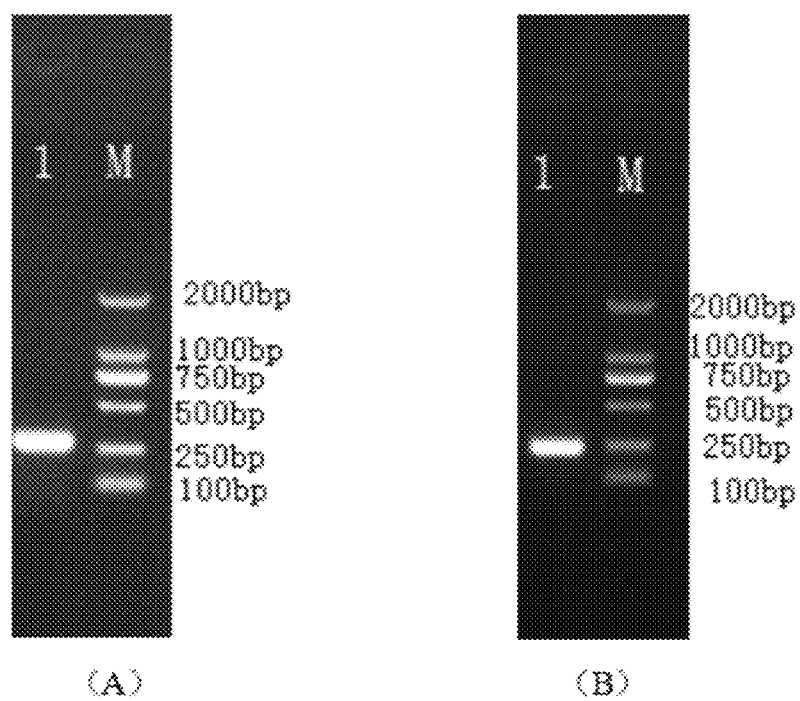
FIG. 1 shows the gel electrophoresis results of segments of *S. chuatsi* IL-6 gene after amplification, wherein (A) agarose gel electrophoresis results of second round PCR of *S. chuatsi* IL-6 gene via cDNA 5' end RACE, lane 1 represents the target fragment; (B) agarose gel electrophoresis results of second round PCR of *S. chuatsi* IL-6 gene via cDNA 3' end RACE, lane 1 represents the target fragment.

The present invention will be explained in more detail below with reference to the drawings and in connection with embodiments. It should be understood that, the exemplary embodiments and description thereof of the invention are used for illustrating the present invention and are not intended to limit the invention I. Clone of IL-6 cDNA Sequence of *S. chuatsi*

1. Amplification of IL-6 5' Terminal Sequence of *S. chuatsi*

(1) Synthesis, Purification and Tailing of the First Strand of cDNA

The first strand of cDNA of IL-6 was synthesized for the extracted total RNA using SUPERSCRIPT II RT enzyme and the primer GSP-IL-6-1. RNase Mix was used to perform RNA removal on the synthesized cDNA. Reverse transcription system was:

| GSP-IL-6-1 | 25 ng |
|---|---|
| Template RNA | 2 ul |
| DEPC-treated water | making up to 15.5 μl |

This system was incubated at 70° C. for 10 min, and immediately placed on ice to cool for 1 min, and then transient centrifugation was performed to collect liquid. The following system was added sequentially:

| 10 × PCR bbuffer | 2.5 μl |
|---|---|
| 25 nM MgCl$_2$ | 2.5 μl |
| 10 nM dNTP mix | 1 ul |
| 0.1M DTT | 2.5 ul |

The reaction system was mixed gently, centrifuged and incubated at 42° C. for 1 min. 1 μl SUPERSCRIPT II RT was added, mixed evenly and incubated at 42° C. for 50 min, at 70° C. for 15 min and then reaction was stopped. After centrifugation, the resulting product was placed at 37° C., and 1 μl of RNase mix was added to react for 30 min and then purification was performed. poly (c) was added at the purified cDNA terminal using TdT enzyme and dCTP, then the product was stored at a low temperate for use.

(2) Quick Amplification of cDNA 5' Ends

The first round PCR amplification was performed on the cDNA to which the dC tail had been added using the primer GSP-IL-6-2. The 5'-RACE system was added in the following order:

| sterilized, distilled water | 31.5 μl |
|---|---|
| 10 × PCR buffer | 5.0 μl |
| 25 mM MgCl$_2$ | 3.0 μl |
| 10 mM dNTP mix | 1.0 μl |
| 10 μM nested GSP-TLR3-2 | 2.0 μl |
| 10 uM Abridged Anchor Primer | 2.0 μl |
| dC-tailed cDNA | 5.0 μl |
| Taq DNA polymerase | 0.5 μl |
| final volume | 50 μl |

The reaction conditions were as follows: pre-denaturation at 94° C. for 2 min, denaturation at 94° C. for 30 s, re-analysis annealing at 55° C. for 30 s, extension at 72° C. for 1 min, 30 cycles, and finally extension at 72° C. for 7 min.

The nested second round PCR amplification was performed using the primer GSP-IL-6-3 and abridged universal amplification primer AUAP, and the system was as follows:

| sterilized, distilled water | 33.5 μl |
|---|---|
| 10 × PCR buffer | 5.0 μl |
| 25 mM MgCl$_2$ | 3.0 μl |
| 10 mM dNTP mix | 1.0 μl |
| 10 μM nested GSP-TLR3-3 | 1.0 μl |
| 10 uM AUAP | 1.0 μl |
| dilution of primary PCR product | 5.0 μl |
| Taq DNA polymerase | 0.5 μl |
| final volume | 50 μl |

The reaction conditions were as follows: pre-denaturation at 94° C. for 2 min, denaturation at 94° C. for 30 s, re-analysis annealing at 59° C. for 30 s, extension at 72° C. for 1 min, 30 cycles, and finally extension at 72° C. for 7 min.

Agarose gel electrophoresis (1.2%) was performed on the product of the second round PCR, the target bands were recycled by gel extraction using Gel Extraction Kit (Sangon Shanghai). The purified PCR product was recycled and cloned to the pMD18-T vector (TaKaRa), and positive clones were selected for sequencing.

2. Amplification of IL-6 3' Terminal Sequence of S. chuatsi (1) Synthesis and Purification of the First Strand of cDNA Reverse transcription was performed on the total extracted RNA using SUPERSCRIPT II RT enzyme and the primer 3'CDS primer A (SMARTer™ RACE cDNA Amplification Kit, Clontech). The used primer was 3'CDS primer A, and the other components and conditions were the same as those of 5' terminal amplification.

(2) Quick Amplification of cDNA Ends

The first round PCR amplification was performed using the primers GSP-IL-6-4 and UPM using the cDNA synthesized previously as a template, and the 3'-RACE reaction system was added in the following order (the reaction conditions were the same as those of the 5' ends amplification):

| | |
|---|---|
| sterilized, distilled water | 31.5 μl |
| 10 × PCR buffer | 5.0 μl |
| 25 mM MgCl$_2$ | 3.0 μl |
| 10 mM dNTP mix | 1.0 μl |
| 10 μM GSP-IL-6-4 | 2.0 μl |
| 10 uM UPM | 2.0 μl |
| dC-tailed cDNA | 5.0 μl |
| Taq DNA polymerase | 0.5 μl |
| final volume | 50 μl |

The PCR product from the first round amplification was diluted 50 times to perform the second round PCR amplification, the other systems were the same as those of the first round PCR amplification other than the primers GSP-IL-6-5 and UPM, and the reaction conditions were the same as those of 5' amplification. Agarose gel electrophoresis (1.2%) was performed on the product of the second round PCR, and the target band was recycled by gel extraction, as shown in FIG. 1. The purified product was cloned to the pMD18-T vector (TaKaRa), and the positive clones were selected for sequencing, the spliced complete sequence of S. chuatsi IL-6 cDNA is shown in SEQ ID NO: 1, and the encoded amino acid sequence of the S. chuatsi IL-6 cDNA is shown in SEQ ID NO: 3.

TABLE 1

Primer Sequences for amplification of IL-6 gene cDNA

| Primers | Sequences (5'-3') | Target |
|---|---|---|
| GSP-IL-6-1 (SEQ ID NO: 4) | CTGGGGCACTCCTTCT | IL-6 5'-Race |
| GSP-IL-6-2 (SEQ ID NO: 5) | AACCTGTGGAGACAAGCC | IL-6 5'-Race |
| GSP-IL-6-3 (SEQ ID NO: 6) | CTGAAGTTGGAGTAAGGGCA | IL-6 5'-Race |
| 3'CDS Primer A (SEQ ID NO: 7) | AAGCAGTGGTATCAACGCAG ACTAC | IL-6 3'-Race |

TABLE 1-continued

Primer Sequences for amplification of IL-6 gene cDNA

| Primers | Sequences (5'-3') | Target |
|---|---|---|
| GSP-IL-6-4 (SEQ ID NO: 8) | CGCCAGCTCCACTACTTCCT TGTCG | IL-6 3'-Race |
| GSP-IL-6-5 (SEQ ID NO: 9) | AAAGGGAGTTCAGAGCAAGT ATGGC | IL-6 3'-Race |
| AUAP (SEQ ID NO: 10) | GGCCACGCGTCGACTAGTAC | universal 5'-Race |
| UPM (SEQ ID NO: 11) | CTAATACGACTCACTATAGG GC | universal 3'-Race |

3. Obtaining of S. chuatsi IL-6 gDNA

Figure 2:
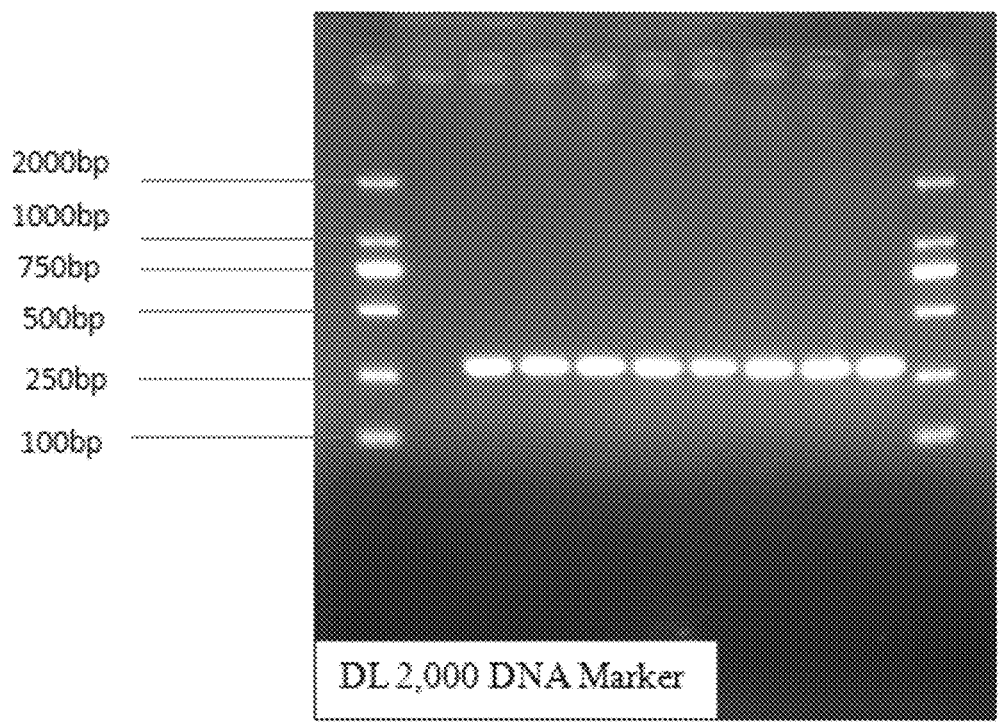
FIG. 2 shows the gel electrophoresis results after PCR amplification of *S. chuatsi* IL-6 gene by adding the primer used by an intron.

With reference to the known IL-6 gDNA structure of other fishes, the specific primers were designed for the spliced complete fragment of S. chuatsi IL-6 cDNA to amplify the intron of IL-6 gene (table 2), wherein the fragment should contain overlapping regions for facilitating the subsequent sequence assembly. The genomic DNA of S. chuatsi was used as a template to perform fragment PCR amplification. The amplification conditions were as follows: pre-denaturation at 94° C. for 5 min, denaturation at 94° C. for 30 s, annealing at 52° C. for 30 s, extension at 72° C. for 1 min, 30 cycles, and finally extension at 72° C. for 7 min. Agarose gel electrophoresis (1.5%) was performed on the PCR product, as shown in FIG. 2, single band was selected and recycled by gel extraction, and ligated to the pUmc-T vector using T vector PCR products cloning Kit(TAKARA), the system (10 μL) was stored overnight at 4° C. The positive clones were selected for sequencing. The obtained sequences were spliced using artificial alignment and DNA-MAN software to get the full-length sequence of S. chuatsi IL-6 gDNA, as shown in SEQ ID NO: 2.

TABLE 2

Primer sequences for amplifying the intron of IL-6 gene

| Primers | Primer sequences (5'-3') |
|---|---|
| IL-6-1F (SEQ ID NO: 12) | CTCAGCATCAGCGGAAACTC |
| IL-6-1R (SEQ ID NO: 13) | TGCCCCTGTTGGCCATACTT |

4. Detection of Disease-Resistant SNP Marker (1) Primers (table 3) were designed according to the sequence of S. chuatsi IL-6 gDNA. The PCR reaction system is shown in table 4.

TABLE 3

Primer sequences for obtaining disease-resistant SNP loci by amplifying S. chuatsi IL-6 gene

| Primers | Primer sequences (5'-3') |
|---|---|
| IL-6-L1F (SEQ ID NO: 14) | AACCCAAAGAGGCAGGTGAC |
| IL-6-L1R (SEQ ID NO: 15) | ACCATCCAATTTCCCTGAGGT |

TABLE 4

PCR reaction system for obtaining disease-resistant SNP
loci by amplifying *S. chuatsi* IL-6 gene

| Components | Volume μl ) |
|---|---|
| Template DNA | 2 |
| Primer R ( 10 μl ) | 1 |
| Primer F ( 10 μl ) | 1 |
| 2 × Easy Taq PCR Super Mix | 25 |
| ddH$_2$O | 21 |
| Total | 50 |

Steps of PCR amplification were as follows: (1) pre-denaturation at 94° C. for 5 min, (2) denaturation at 94° C. for 30 s, (3) annealing at 52° C. for 30 s, (4) extension at 72° C. for 1 min, 30 cycles, and (5) extension at 72° C. for 10 min, (1) 4° C. end of the reaction.

Figure 3:
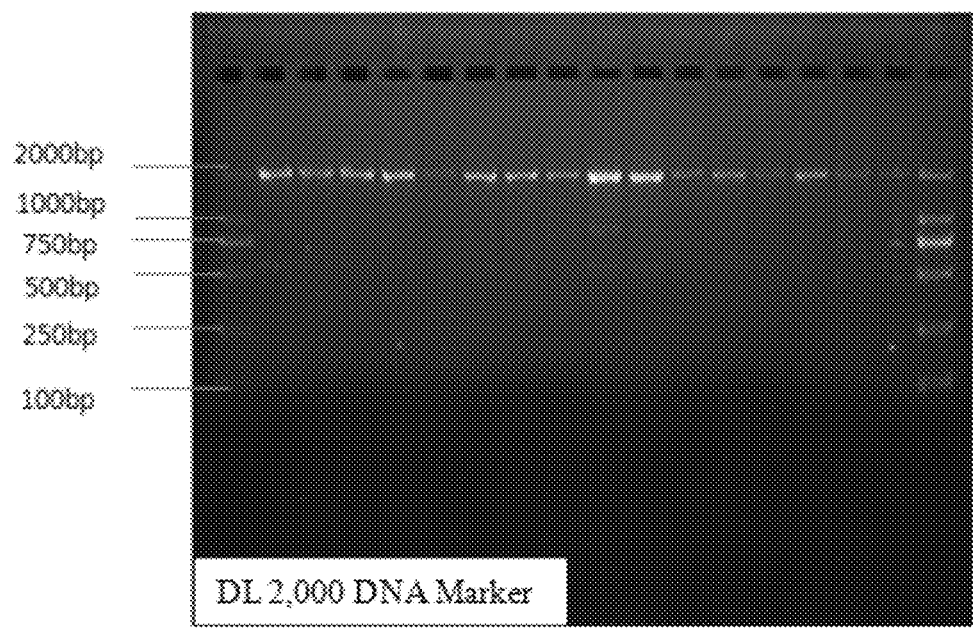
FIG. 3 shows the gel electrophoresis results after PCR amplification of SNP locus detection of *S. chuatsi* IL-6 gene.
Figure 4:
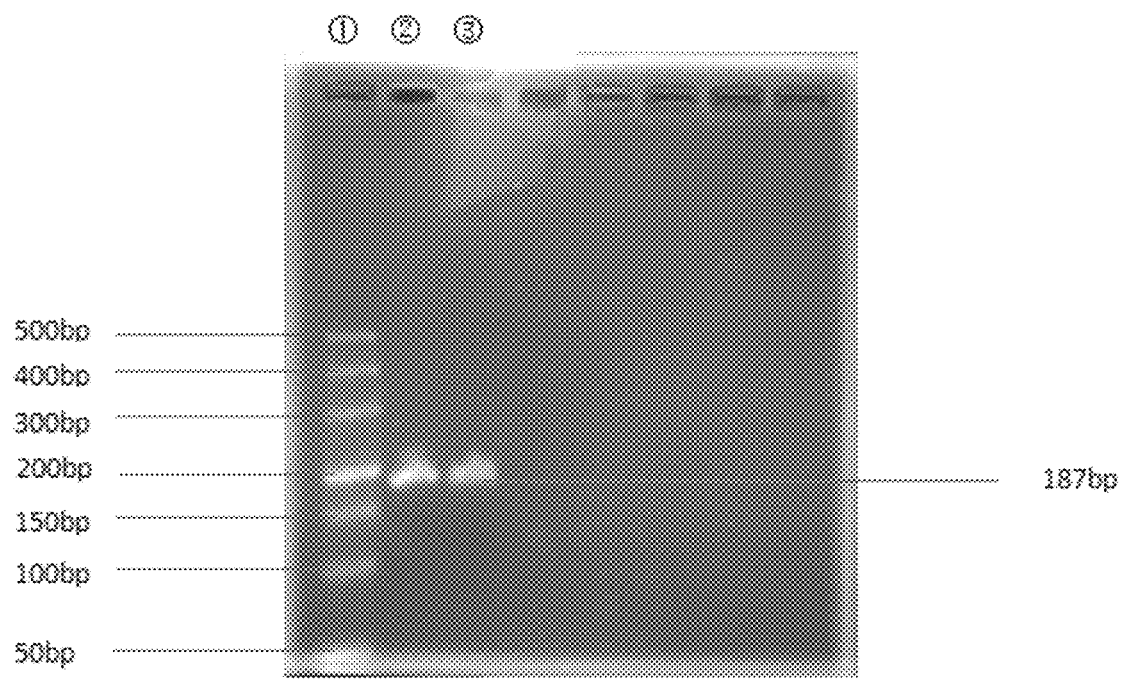
FIG. 4 shows the PCR detection results of infectious spleen and kidney necrosis virus (ISKNV) for head kidney tissue of *S. chuatsi*, wherein lane ① represents the band after DL500 Mark electrophoresis; both lane ② and lane ③ represent a single and bright ISKNV virus nucleotide-specific band (187 bp) obtained by performing PCR amplification and electrophoresis using a template prepared by head kidney tissue homogenate of *S. chuatsi* in the ISKNV virus infection group; the other lanes represent non-specific bands obtained by performing PCR amplification and electrophoresis using a template prepared by head kidney tissue homogenate of *S. chuatsi* in the ISKNV virus infection group.

(2) Agarose gel electrophoresis (1.5%) was performed on the PCR product to get the PCR amplification product, as shown in FIG. 3, and then immediately sequenced after gel extraction.

The multiple sequence alignment was performed on the sequencing results using DNAMAN software, to find out the SNPs loci relevant to the virus disease resistance. Then DNA sequencing chromatogram was observed via Chromas software, single peak was a homozygotic SNP locus, and the nested peak was a heterozygous SNP locus.

II Detection Results of Disease-Resistant SNP Marker Based on *S. chuatsi* IL-6 Gene The same population of *S. chuatsi* was bred under the same feeding conditions, and after breeding for about two months, 100 Mandarin fish were randomly selected for challenge experiments from the cultured population. Each fish was intraperitoneally injected with infectious spleen and kidney necrosis virus (ISKNV) (also known as iridescent virus), 10×TCID50 ISKNV. After observing for 10 days, it was observed that the disease symptoms are the same as those of the ISKNV infection in the natural environment. The diseased fish swam slowly on the water surface, or evenly floated on the water surface, the body surface was undamaged and the colour of body was white. The fish gills were ischemic whitish. By means of anatomy, it was found that there were ascites in enterocoelia, the liver, the stomach wall and the intestinal wall were congestive, and there was yellow effusion in intestinal tract. While the disease-resistant fish were normal all the time. The PCR detection indicated that the head kidney of the diseased *S. chuatsi* were ISKNV-positive, this shows that the death was caused by ISKNV infection.

9 undiseased fish and 3 diseased fish (marked as E05, H07, A07) were selected, and a small quantity of tail fin was cut and placed in absolute ethyl alcohol and stored at 4° C., respectively. In terms of the detection method of disease-resistant SNP marker as described in above examples, the PCR amplification product was obtained, as shown in FIG. 3, after gel extraction, sequencing was performed and multiple sequence alignment was performed by DNAMAN, and the SNP locus associated with virus disease resistance was found at 233 bp of a nucleotide sequence fragment, as shown in FIG. 5.

Figures 5, 6:
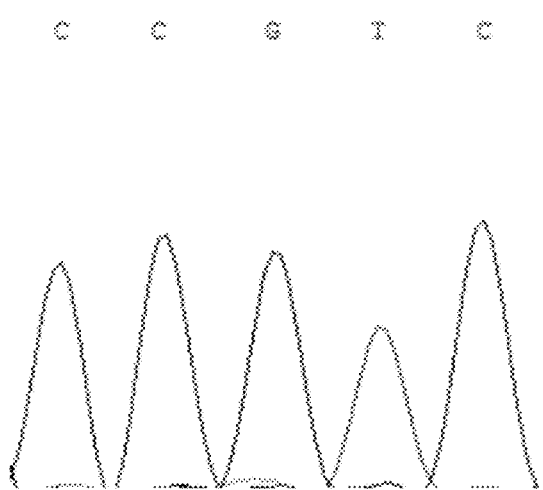
FIG. 5 shows a screen shot of comparison results of IL-6 DNA reverse complementary sequence of 22 groups of *S. chuatsi* samples, wherein the base G is mutated to base A in three samples.
FIG. 6 shows the peak profile generated by sequencing IL-6 DNA of a *S. chuatsi* sample, wherein G homozygote is not mutated in IL-6 DNA of *S. chuatsi* sample of this figure.
Figure 7:
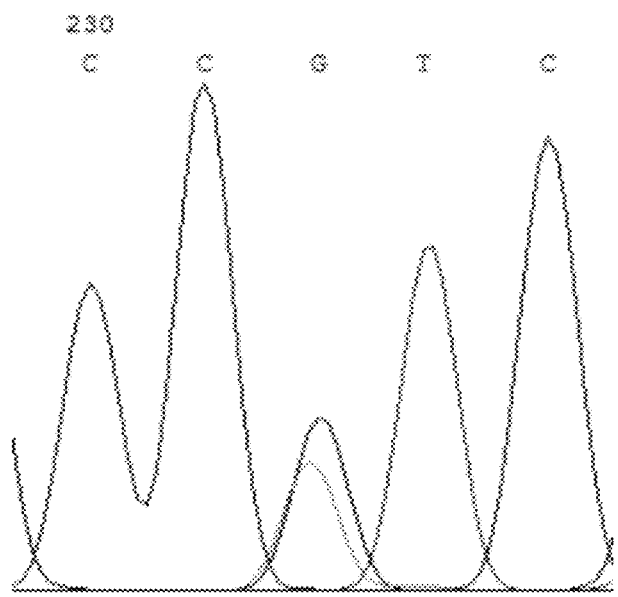
FIG. 7 shows the peak profile generated by sequencing IL-6 DNA of a *S. chuatsi* sample, wherein G heterozygote is not mutated in IL-6 DNA of a *S. chuatsi* sample of this figure.
Figure 8:
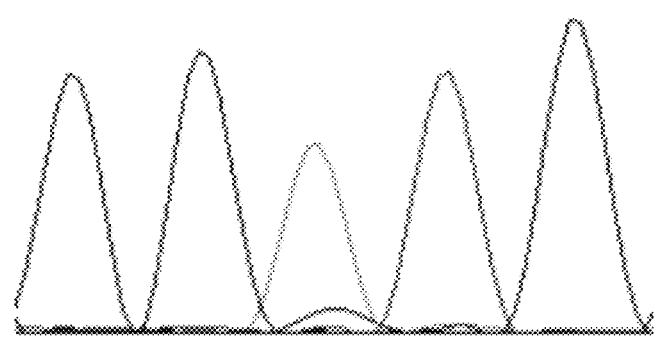
FIG. 8 shows the peak profile generated by sequencing IL-6 DNA of a *S. chuatsi* sample, wherein A homozygote is mutated in IL-6 DNA of *S. chuatsi* sample of this figure.

The peak profile of suspected mutant base at 233 bp in the above sequence was observed by Chromas software, as shown in FIG. 6, FIG. 7, and FIG. 8. At the corresponding bases G and A, the peaks are single and there are no impurity peaks. From this, the base at 233 bp is mutated from G to A, that is G233A. Because the mutation was in the Reverse Complement sequence of DNA, that is, a base sequence AGCTCTTTTGCCGTCGACAAGGAA (SEQ ID NO: 16) (FIG. 5) adjacent to 233 bp of a nucleotide sequence fragment, reverse complement to a base sequence adjacent to 1733 bp of IL-6 gDNA sequence (SEQ ID NO: 2.), in the original DNA sequence, SNP locus was at C1744T. The three samples with base mutation (E05, H07, A07) (AGCTCTTTTGCCATCGACAAGGAA (SEQ ID NO: 17) (FIG. 5)) all were *S. chuatsi* susceptible to virus. Consequently, the mutation from G to T was generated at 1744 bp of SNP of IL-6 gene of *S. chuatsi* susceptible to virus. The base at 1744 bp of *S. chuatsi* susceptible to virus is T, and the base at 1744 bp of antivirus *S. chuatsi* is C, the virus is infectious spleen and kidney necrosis virus (ISKNV). By means of this method, the antivirus *S. chuatsi* can be distinguished from *S. chuatsi* susceptible to virus.

The above preferred embodiments are described for illustration only, and are not intended to limit the scope of the invention. It should be understood, for a person skilled in the art, that various improvements or variations can be made therein without departing from the spirit and scope of the invention, and these improvements or variations should be covered within the protecting scope of the invention.

What is claimed is:

1. A method comprising the steps of:
   (1a) amplifying a *Siniperca chautsi* sample with the primer pair consisting of SEQ ID NO: 12 and SEQ ID NO: 13 or
   (1b) amplifying a *Siniperca chautsi* sample with the primer pair consisting of SEQ ID NO: 14 and SEQ ID NO: 15, and then after amplification step (1a) or (1b),
   (2) sequencing the amplification product.

2. A method for detecting a SNP marker in a *Siniperca chautsi* IL-6 gene comprising the steps of:
   (1a) amplifying a *Siniperca chautsi* sample with the primer pair consisting of SEQ ID NO: 12 and SEQ ID NO: 13 or
   (1b) amplifying a *Siniperca chautsi* sample with the primer pair consisting of SEQ ID NO: 14 and SEQ ID NO: 15, and then after amplification step (1a) or (1b),
   (2) sequencing the amplification product and detecting a C at the position corresponding to nucleotide 1744 of SEQ ID NO: 2, wherein the C nucleotide indicates resistance to an infectious spleen and kidney necrosis viral infection.

3. A method for detecting a SNP marker in a *Siniperca chautsi* IL-6 gene comprising the steps of
   (1a) amplifying a *Siniperca chautsi* sample with the primer pair consisting of SEQ ID NO: 12 and SEQ ID NO: 13 or
   (1b) amplifying a *Siniperca chautsi* sample with the primer pair consisting of SEQ ID NO: 14 and SEQ ID NO: 15, and then after amplification step (1a) or (1b),
   (2) sequencing the amplification product and detecting a T at the position corresponding to nucleotide 1744 of SEQ ID NO: 2, wherein the T nucleotide indicates susceptibility to an infectious spleen and kidney necrosis viral infection.

* * * * *